United States Patent [19]
Wu et al.

[11] Patent Number: 5,770,706
[45] Date of Patent: *Jun. 23, 1998

[54] SNAP-CURE EPOXY ADHESIVES

[75] Inventors: Bing Wu, Marina Del Rey, Calif.; Quinn K. Tong, Belle Mead; Rose Ann Schultz, Princeton, both of N.J.

[73] Assignee: National Starch and Chemical Investment Holding Corporation, Wilmington, Del.

[*] Notice: The term of this patent shall not extend beyond the expiration date of Pat. Nos. 5,646,315 and 5,703,195.

[21] Appl. No.: 656,621

[22] Filed: May 31, 1996

Related U.S. Application Data

[63] Continuation-in-part of Ser. No. 482,540, Jun. 7, 1995, abandoned.

[51] Int. Cl.$^6$ .............................. C08L 63/00; C08K 3/10
[52] U.S. Cl. ......................... 523/429; 523/459; 528/103
[58] Field of Search .................................. 523/429, 459; 528/103

[56] References Cited

U.S. PATENT DOCUMENTS

| | | | |
|---|---|---|---|
| 3,267,172 | 8/1966 | Arnold | 528/103 |
| 3,488,404 | 1/1970 | Parker, Jr. | 528/103 |
| 5,043,102 | 8/1991 | Chen et al. | 523/429 |
| 5,536,855 | 7/1996 | Schultz et al. | 549/539 |
| 5,646,315 | 7/1997 | Schultz et al. | 549/554 |
| 5,703,195 | 12/1997 | Schultz et al. | 528/103 |

FOREIGN PATENT DOCUMENTS

| | | | |
|---|---|---|---|
| 0 028 024 | 5/1981 | European Pat. Off. | C07D 303/16 |
| 0 205 402 | 12/1986 | European Pat. Off. | C07D 303/24 |
| 0 397 317 | 11/1990 | European Pat. Off. | C07D 303/24 |
| 0 459 591 | 12/1991 | European Pat. Off. | C08G 59/38 |
| 63-202676 | 8/1988 | Japan . | |
| 1017612 | 1/1963 | United Kingdom . | |

OTHER PUBLICATIONS

Lee et al., "Handbook of Epoxy Resins", McGraw–Hill Book Co., p. 10/17 (1982 Reissue).

*Primary Examiner*—Donald R. Wilson
*Attorney, Agent, or Firm*—Jane E. Gennaro

[57] ABSTRACT

This invention relates to adhesive formulations, which can be snap-cured without loss of adhesive strength (as measured by die shear strength) and flexibility (as measured by radius of curvature), comprising 20–80 parts by weight of a flexible epoxy resin and 80–20 parts by weight of an aromatic O-glycidyl ether (to a total 100 parts), a curing catalyst, and optionally one or more fillers.

24 Claims, No Drawings

SNAP-CURE EPOXY ADHESIVES

This application is a continuation-in-part of Ser. No. 08/482,540, filed 07 Jun. 1995, now abandoned.

FIELD OF THE INVENTION

This invention is directed to flexible epoxy adhesives that can be rapidly cured for use in microelectronics applications.

BACKGROUND OF THE INVENTION

One step in the manufacture of semiconductor integrated circuits is the bonding of a silicon chip or die with an adhesive to a copper frame from which extend metal conductor leads. The bonded die and lead frame assembly is encapsulated within a polymeric sealant and connected to external circuitry by way of the metal conductor leads that extend through the encapsulation.

Epoxy compounds are preferred as the die attach or encapsulating adhesive due to their superior adhesive strength. The epoxies conventionally used are the aromatic epoxies, due to their strength, but these are inherently rigid and brittle. During the manufacturing process the adhesives and substrates are subjected to repeated thermal cycling. If the adhesives and substrates have widely disparate coefficients of thermal expansion, the stress of thermal cycling can lead to adhesive failure, substrate warpage, or fracture of the die. Thus, a crucial requirement for an adhesive destined for microelectronics use is that it be strong and flexible to absorb the stress of thermal cycling.

A second crucial criterion is that the adhesives be capable of rapidly curing to meet the speeds of assembly line processing. The fast cure times required, typically 30–60 seconds at about 200° C., are known as snap-cure. This combination of criteria, adhesive strength, flexibility, and ability to be snap-cured, is difficult to attain in one adhesive.

It is also crucial that the epoxy formulations be free of ionic contamination, particularly sodium and chloride ions, and free of bonded chlorine. These contaminants can cause corrosion of the metal leads in semiconductor devices and the ultimate failure of the devices.

To add flexibility, epoxies can be co-reacted with an aliphatic flexibilizer; this, however, reduces adhesive strength because the level of aromatic moieties is lowered. The addition of a flexibilizer also reduces snap-cure because the flexibilizer has a high molecular weight per epoxy. Moreover, when the aliphatic and aromatic epoxies are cured, they may not co-react due to a difference in reactivity rates; low molecular weight compounds may volatilize out before cure, and high molecular weight compounds may not completely cure. This combination of factors, sometimes even a problem for slow cure formulations, is fatal for achieving snap-cure.

As a possible solution to some of these problems, it is known to combine aromatic moieties with aliphatic moieties in the backbone of the same polymer, but the currently available polymers of this type have a high ratio of aromatic to aliphatic moieties, which results in a loss of flexibility. Additionally, the method of preparation of these materials results in high chlorine contamination, which is deleterious in microelectronics applications. The polymers also have high viscosities, which requires the addition of a solvent as a diluent. During snap-cure, the curing is sometimes faster than complete solvent volatilization, which leads to voids in the cured adhesive, and potential failure of the microelectronics chip or device. Thus, low viscosity materials, which eliminate the need for solvent, are preferred.

These problems make formulation of snap-cure adhesives difficult and create a continuing need for snap-curable adhesives that have strength and flexibility.

SUMMARY OF THE INVENTION

This invention relates to adhesive formulations, which can be snap-cured without loss of adhesive strength (as measured by die shear strength) and flexibility (as measured by radius of curvature), comprising 20–80 parts by weight of a flexible epoxy resin and 80–20 parts by weight of an aromatic O-glycidyl ether (to a total 100 parts), a curing catalyst, and optionally one or more fillers.

The flexible epoxies are prepared by a synthetic route that avoids the use of epichlorohydrin resulting in low levels of ionic contaminated sources (including sodium ion, chloride ion, and organic bound chlorine), less than about 0.1% by weight, compared to prior art compositions, which contain impurities at higher levels, especially when the compositions are not subjected to stringent purification methods that significantly reduce yields. Moreover, the synthetic routes permit the preparation of discreet chemical structures, rather than mixes of various resins.

In another embodiment the adhesive formulation will further contain 20–50 parts per hundred parts of the epoxy resins of a phenolic hardener, which serves to improve the adhesion strength of the formulation after exposure to moisture and thermal shock and to prevent bleeding of the flexible epoxy out of the formulation.

The flexible epoxy of the formulation may be any liquid epoxy having a center flexible portion of $C_4$–$C_{50}$ polyether, or $C_4$–$C_{50}$ hydrocarbon, that may contain $C_5$–$C_8$ cyclic units (including aromatic units), end-capped at each terminus with one or more epoxy groups, and having a cured $T_g$ of less than 70° C. (peak measured in Tan-delta by Dynamic Mechanical Analysis) and preferably less than room temperature.

The aromatic O-glycidyl ether (aromatic epoxy) will have one or more aromatic rings with one or more O-glycidyl ether groups. The aromatic rings may also be substituted with one or more $C_1$–$C_3$ groups. The aromatic epoxies will have an epoxy equivalent weight (WPE, weight per epoxy) of 200 or less, and can be derived from the corresponding phenolic hardeners. Exemplary aromatic epoxies are bisphenol-F diglycidyl ether, bisphenol-A diglycidyl ether, resorcinol diglycidyl ether, and the epoxy phenol novolaks.

The phenolic hardener will have one or more hydroxyl groups per aromatic ring (from which are derived the aromatic epoxies herein). Exemplary phenolic hardeners are the commercially available phenol novolak resins, bisphenol-F, bisphenol-A, and resorcinol.

In general any effective curing catalyst in an effective catalytic amount can be used. The preferred curing catalyst is an imidazole catalyst, and typically is present in an amount of about 5 parts per hundred parts resin. Preferable imidazole catalysts are imidazole, 2-ethylimidazole, 2-ethyl-4-methylimidazole, 2-phenylimidazole, 2-phenyl-4-methylimidazole, and 2-undecylimidazole.

The filler may be any of the thermally or electrically conductive materials known to be suitable for microelectronics applications, used in any effective amount. For many applications, the preferred filler is silver flakes, although other electrically or thermally conductive fillers may be used, and is preferably present in an amount of about 25% by volume of the adhesive formulation.

DETAILED DESCRIPTION OF THE INVENTION

The preferred flexible epoxy will have an oligomeric backbone of alkylene or alkyleneoxy repeat units, terminated with an aromatic moiety bearing one or more epoxy functionalities. The compounds will have no more than two aromatic moieties, which exist only at the termini, no more than two hydroxyl groups per molecule, and will have one of the following general structural formulas:

I.

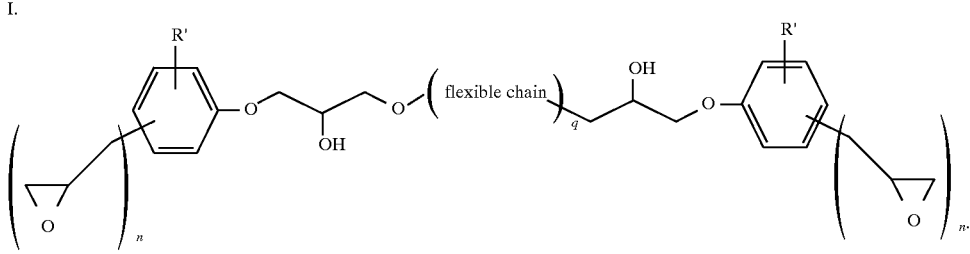

where flexible chain is CH2CH2CH2CH2O when q=1–6
or where flexible chain is CH2CH2O when q=3–10

II.

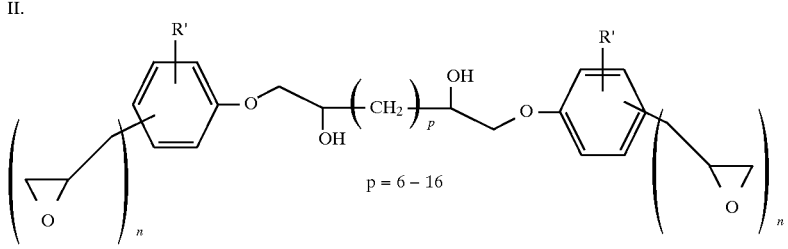

III.

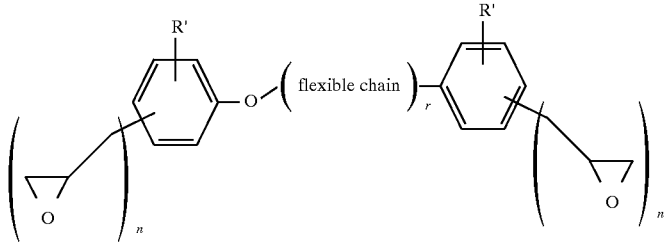

where flexible chain is CH2CH2CH2CH2O when r=1–10
or where flexible chain is CH2CH2O when r=3–10
or where flexible chain is CH2 when r=10–20
in which R' is H, $C_{1-18}$alkyl, $C_{1-5}$alkoxy or aryl or alkylaryl, $C_{1-5}$perfluoroalkyl, or $C_{1-5}$acyl;

n is an integer 1–3; the flexible chain is as described for each structure; and p, q, and r are integers as described for each structure.

As used here, alkyl refers to a hydrocarbon group derived from an alkane and have the generic formula $C_nH_{2n+1}$; alkoxy refers to an alkyl group also containing oxygen; aryl refers to a group having the ring structure characteristic of benzene; alkylaryl refers to a group containing both alkyl and aryl structures; perfluoroalkyl refers to an alkyl group in which one or more of the hydrogens are substituted with fluorine; and acyl refers to an organic acid group in which the OH of the carboxyl group is replaced by some other substituent, in this case, the phenyl ring to which it is attached.

The flexibilized epoxy resins may be prepared by any suitable synthetic method that leaves the product free of ionic contamination. The preferred synthetic routes are those that avoid the use of epichlorohydrin, and comprise the steps of (a) preparing an olefinic precursor by attaching an alkylene or alkyleneoxy chain to a phenoxy compound bearing olefinic groups, and (b) oxidizing the olefinic groups to the corresponding epoxides.

In step (a), the flexible alkylene or alkyleneoxy chain is end terminated with a functional group that is activated toward nucleophilic substitution. Preferably the functional group is an epoxy, chloro, sulfonate, or toluenesulfonate. The flexible chain is derivatized by nucleophilic addition of a phenolate compound displacing the chloride, sulfonate, or alkoxide (from epoxy ring opening) functional group. The phenolate is prepared from the reaction of sodium hydroxide or other alkali metal hydroxide with a phenol compound having only one hydroxyl group, which assures that the nucleophilic substitution can occur only once and discrete chemical structures result (that is, not mixtures of products). The phenol compound is also substituted with an olefin moiety, preferably an allyl group, which is inert to nucleophilic substitution, and serves as the site for the final epoxide product. In step (b), the olefin on the phenol group is converted to the oxirane (epoxide).

Preparation of the Olefinic Precursors

The olefinic precursors to the epoxy compound preferably may be prepared by one of the following generally described methods. More specific detail for each method is provided in the examples.

I. A diglycidyl compound of an alkylene or alkyleneoxy chain, of appropriate length to conform in the final product to one of the above described general structures, may be reacted with a phenolic compound bearing one or more olefinic groups in the presence of a catalyst effective for catalyzing condensation reactions between phenolic compounds and oxiranes.

Preferred diglycidyl compounds are 1,4-butanediol diglycidyl ether; 1,12-dodecanediol diglycidyl ether; polyethylene glycol digylcidyl ether, poly(tetra-methylene glycol) diglycidyl ether, and polypropylene glycol diglycidyl ether, or polyglycol copolymers, in which the polyglycol portion of the molecule has a molecular weight less than or equal to 2000 daltons; 1,2,9,10-diepoxydecane, 1,2,13,14-diepoxytetradecane, and similar compounds; and the diglycidyl ether of poly(caprolactone)diol.

Preferred olefin functionalized phenolic compounds are 2-allylphenol; 2,6-diallylphenol; 2,4-diallylphenol; 4-allyl-2-methoxyphenol; 2-allyloxyphenol; and other similar phenolic compounds. The phenolic compound can be used in excess to effect a high degree of reaction with the diglycidyl compound and the excess can be removed from the product by distillation. The phenolic compound may also be substituted with groups that do not interfere with either of the two steps involved in the formation of the product.

Preferred catalysts are quaternary ammonium or phosphonium salts of chloride, bromide, hydrogen sulfate, acetate, and other known catalysts, such as, triphenylphosphine. More preferred catalysts are the quaternary ammonium salts with lower alkyl constituents, particularly tetramethyl ammonium chloride.

II. An alkylene or alkyleneoxy chain, of appropriate length to conform in the final product to one of the above described general structures, and bearing a leaving group, such as, chloride, bromide, iodide, or tosylate, at the termini of the chain, may be reacted with an alkali or alkaline earth metal salt of a phenoxide compound bearing olefinic groups.

The alkylene or alkyleneoxy compound bearing the leaving group generally is derived from the corresponding alcohol by conversion of the hydroxyl group into a leaving group using known reactions. For example, an alkylene or alkyleneoxy chloride can be generated from the alcohol by reaction with $SOCl_2$. The tosylate can be generated from the alcohol by reaction with tosyl chloride in the presence of base. Examples of suitable alcohol terminated alkylene or alkyleneoxy chains include 1,4-butanediol; 1,12-dodecanediol; polycaprolactone diol; polyethylene glycol; polyglycol copolymers; and 1,10-decanediol.

The olefin functionalized phenoxide compound is generated from the corresponding phenolic compound by the action of an alkali or alkaline earth metal hydroxide in the presence of an azeotroping solvent. These reactions are well known in the art. Suitable azeotroping solvents include toluene, xylene, p-cymene, and similar solvents.

After the precursors are formed, the olefin is oxidized by any method effective to provide the corresponding epoxy. Various methods are described in the literature for effectively carrying out the oxidation process, and include the use as an oxidant of organic peracids, such as peracetic acid or trifluoroperacetic acid; peroxyimidic acids; dioxirane compounds like dimethyldioxirane; inorganic peracids, such as peroxytungstate systems; metal-catalyzed systems, such as methyltrioxorhenium and hydrogen peroxide, titanium-catalyzed t-butylhydroperoxide, and manganese-salen catalyzed oxidations.

The preferred epoxidation methods use inorganic peracids, peracetic acid, and peroxyimidic acids as the primary oxidant. More specific detail for each method is provided in the examples.

The preferred inorganic peracids are based on tungstic acid, phosphotungstic acid, and similar compounds, using hydrogen peroxide as the secondary oxidant. The oxidation process is enhanced by employing a two phase aqueous/organic system and a quaternary ammonium or phosphonium salt as the phase transfer catalyst.

Peracetic acid in acetic acid may also be used successfully as the oxidant. Although many solvents are suitable for this oxidation, the rate is faster in chlorinated solvents, such as, dichloroethane. In this process, as the reaction is pushed to complete conversion, the accumulating acetic acid begins to attack the oxirane. The result is a product with a lower oxirane content (higher WPE), and higher viscosity than if the oxidizing agent is an inorganic peracid in the presence of a quaternary onium salt.

The use of peroxyimidic acid as the oxidant provides the advantage that the byproduct is acetamide, which is innocuous to the oxirane. A preferred peroxyimidic acid is derived from acetonitrile and hydrogen peroxide. The optimum conditions for the peroxyimidic acid oxidation include the use of $KHCO_3$, reaction temperature near 40° C., and optionally, the use of an aqueous sponge, such as, 2,2-dimethoxypropane.

EXAMPLES

To test for ability to achieve snap cure, adhesive formulations containing varying amounts of aromatic epoxy, flexible epoxy, and phenolic hardener, with curing catalyst, were prepared and used to bond 80×80 mil$^2$ silicon dies to copper lead frames. These assemblies were cured on a hot plate at 175° C. or 225° C. for one minute. The degree of cure was measured by DSC analysis and the formulation was deemed to achieve snap-cure if the degree of cure was 95% or greater.

For each adhesive formulation, the aromatic and flexible epoxy mix totaled 100 parts by weight, and the phenolic hardener varied from 0–50 parts per hundred parts epoxy resin mix (pphr). The catalyst was added in the amount of 5 pphr, and was either 2-ethyl-4-methylimidazole (2E4MZ) or 2-phenyl-4-methylimidazole (2P4MZ). The compositions for each formulation are given in the example tables.

The formulations were prepared as follows: the phenolic hardener was dissolved with heating (approximately 130° C.) in the flexible epoxy; the imidazole catalyst was dissolved in the aromatic epoxy; these two mixtures were blended together and the blend mixed with 25% by volume silver flakes. This mixture was degassed under vacuum at room temperature for 15–20 minutes, and allowed to sit at room temperature with frequent stirring for 60 minutes before being applied to the silicon dies.

The aromatic epoxies used in the formulations were:

a bisphenol-F epoxy resin manufactured by Shell Chemical Company, sold under the tradename EPON 862 (EPON 862), having the structure:

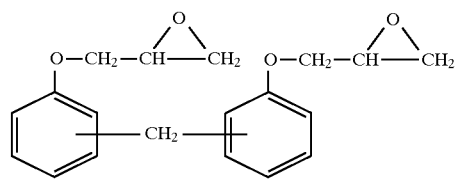

a bisphenol-A epoxy resin, sold under the tradename EPON 825, a product of Shell Chemical Company, having the structure:

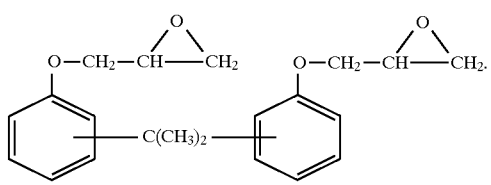

an epoxy designated EPOXY Y, having the structure:

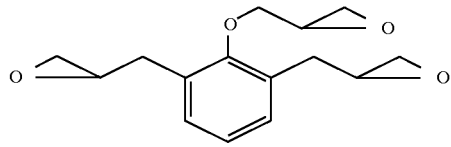

The flexible epoxies used in the formulations were:

a flexible diepoxy synthesized from a dimer acid and having a 36 carbon chain between two epoxy end groups, designated EPOXY X;

a proprietary epoxy designated EPOXY C, having the structure:

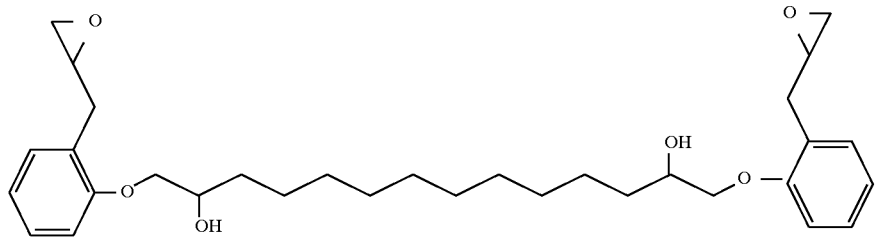

a proprietary epoxy designated EPOXY D, having the structure:

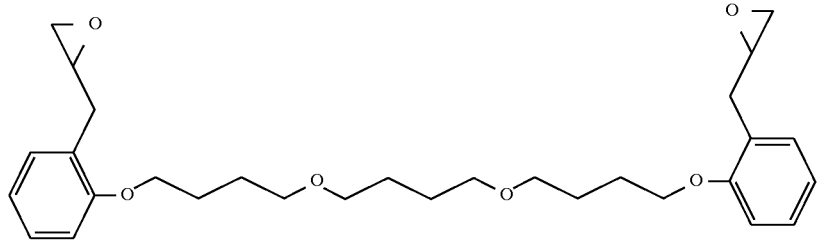

a proprietary epoxy designated EPOXY E, having the structure:

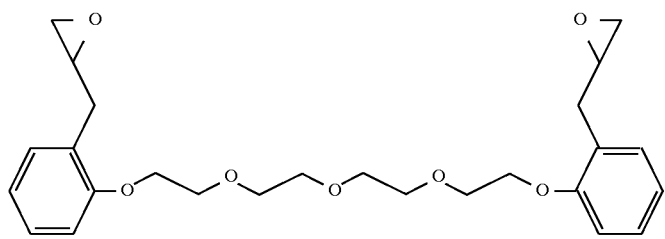

The phenolic hardeners used in the formulations were:

a phenolic novolak resin (NOVOLAK) sold as HRJ-1166, a phenol formaldehyde condensate from Schenectady Chemical, resorcinol, and bisphenol-A.

The results are presented in the following tables.

Example I

Effect of Aromatic Epoxy

The data in Table I show: a formulation containing no phenolic hardener and with a low level of aromatic epoxy to flexible epoxy (20 parts aromatic to 80 parts flexible) does not achieve snap cure at 225° C.; when the aromatic epoxy is present at higher levels (40:60, aromatic:flexible) the formulation will achieve snap-cure, even at the lower temperature of 175° C.

TABLE I

| EPOXY MIX parts by weight aromatic flexible | | IMIDA-ZOLE 5 pphr | PHENOLIC HARDENER pphr | | CURING CONDI-TIONS | DEGREE OF CURE (%) |
|---|---|---|---|---|---|---|
| EPON 862 | 20 | 2E4MZ | NOVOLAK | 0 | 225° C./ 1 min | 70 |
| EPOXY X | 80 | | | | | |
| EPON 862 | 40 | 2E4MZ | NOVOLAK | 0 | 225° C./ 1 min | 98 |
| EPOXY X | 60 | | | | | |
| EPON 862 | 60 | 2E4MZ | NOVOLAK | 0 | 175° C./ 1 min | 100 |
| EPOXY X | 40 | | | | | |
| EPON 862 | 80 | 2E4MZ | NOVOLAK | 0 | 175° C./ 1 min | 100 |
| EPOXY X | 20 | | | | | |

Example II

Effect of Phenolic Hardener

The data in Table II show: formulations containing the higher levels of flexible epoxy (20:80, aromatic:flexible) can be snap-cured by increasing the level of phenolic hardener; the addition of phenolic hardener promotes rapid cure and allows the aromatic:flexible formulations at 40:60 to be fully snap-cured at lower temperatures; at the higher cure temperature, and higher level of epoxy aromatic, the phenolic hardener is not needed for snap-cure.

TABLE II

| EPOXY MIX parts by weight aromatic flexible | | IMIDA-ZOLE 5 pphr | PHENOLIC HARDENER pphr | | CURING CONDI-TIONS | DEGREE OF CURE (%) |
|---|---|---|---|---|---|---|
| EPON 862 | 20 | 2E4MZ | NOVOLAK | 0 | 225° C./ 1 min | 70 |
| EPOXY X | 80 | | | | | |
| EPON 862 | 20 | 2E4MZ | NOVOLAK | 10 | 225° C./ 1 min | 98 |
| EPOXY X | 80 | | | | | |
| EPON 862 | 20 | 2E4MZ | NOVOLAK | 20 | 225° C./ 1 min | 100 |
| EPOXY X | 80 | | | | | |
| EPON 862 | 20 | 2E4MZ | NOVOLAK | 30 | 225° C./ 1 min | 100 |
| EPOXY X | 80 | | | | | |
| EPON 862 | 20 | 2E4MZ | NOVOLAK | 40 | 225° C./ 1 min | 100 |
| EPOXY X | 80 | | | | | |
| EPON 862 | 20 | 2E4MZ | NOVOLAK | 50 | 225° C./ 1 min | 100 |
| EPOXY X | 80 | | | | | |
| EPON 862 | 40 | 2E4MZ | NOVOLAK | 0 | 225° C./ 1 min | 98 |
| EPOXY X | 60 | | | | | |
| EPON 862 | 40 | 2E4MZ | NOVOLAK | 10 | 225° C./ 1 min | 100 |
| EPOXY X | 60 | | | | | |
| EPON 862 | 40 | 2E4MZ | NOVOLAK | 20 | 225° C./ 1 min | 100 |
| EPOXY X | 60 | | | | | |
| EPON 862 | 40 | 2E4MZ | NOVOLAK | 30 | 225° C./ 1 min | 100 |
| EPOXY X | 60 | | | | | |
| EPON 862 | 40 | 2E4MZ | NOVOLAK | 0 | 175° C./ 1 min | 65 |
| EPOXY X | 60 | | | | | |
| EPON 862 | 40 | 2E4MZ | NOVOLAK | 15 | 175° C./ 1 min | 98 |
| EPOXY X | 60 | | | | | |
| EPON 862 | 40 | 2E4MZ | NOVOLAK | 20 | 175° C./ 1 min | 100 |
| EPOXY X | 60 | | | | | |
| EPON 862 | 40 | 2E4MZ | NOVOLAK | 40 | 175° C./ 1 min | 98 |
| EPOXY X | 60 | | | | | |

Example III

Effect of Curing Temperature, Effect of Catalyst and Variations in Composition of Flexible Epoxies The data in Table III show: at the higher levels of flexible epoxy, higher curing temperatures are needed to obtain maximum snap-cure; either of the two exemplary catalysts will effect an efficient snap-cure; the composition of the flexible epoxies can be varied and snap-cure achieved.

TABLE III

| EPOXY MIX parts by weight aromatic flexible | | IMIDA-ZOLE 5 pphr | PHENOLIC HARDENER pphr | | CURING CONDI-TIONS | DEGREE OF CURE (%) |
|---|---|---|---|---|---|---|
| EPON 862 | 20 | 2E4MZ | NOVOLAK | 20 | 175° C./ 1 min | 95 |
| EPOXY X | 80 | | | | 225° C./ 1 min | 100 |
| EPON 862 | 20 | 2P4MZ | NOVOLAK | 40 | 175° C./ 1 min | 100 |
| EPOXY X | 80 | 2E4MZ | | | 225° C./ 1 min | 100 |
| EPON 862 | 20 | 2P4MZ | NOVOLAK | 40 | 175° C./ 1 min | 94 |
| EPOXY C | 80 | | | | 225° C./ 1 min | 100 |
| EPON 862 | 20 | 2P4MZ | NOVOLAK | 40 | 175° C./ 1 min | 86 |
| EPOXY D | 80 | | | | 225° C./ 1 min | 100 |
| EPON 862 | 20 | 2P4MZ | NOVOLAK | 40 | 175° C./ 1 min | 94 |
| EPOXY E | 80 | | | | 225° C./ 1 min | 100 |

Example IV

Variations in Composition of Aromatic Epoxies and Phenolic Hardeners

The data in Table IV show: snap-curable adhesive formulations can be achieved with various compositions of aromatic epoxies and phenolic hardeners.

TABLE IV

| EPOXY MIX parts by weight aromatic flexible | | IMIDA-ZOLE 5 pphr | PHENOLIC HARDENER pphr | | CURING CONDI-TIONS | DEGREE OF CURE (%) |
|---|---|---|---|---|---|---|
| EPOXY Y | 20 | 2P4MZ | NOVOLAK | 40 | 225° C./ 1 min | 100 |
| EPOXY X | 80 | | | | | |
| EPOXY Y | 20 | 2P4MZ | NOVOLAK | 60 | 225° C./ 1 min | 100 |
| EPOXY X | 80 | | | | | |
| EPOXY Y | 20 | 2P4MZ | Resorcinol | 30 | 225° C./ 1 min | 100 |
| EPOXY X | 80 | | | | | |
| EPOXY Y | 20 | 2P4MZ | Bisphenol A | 30 | 225° C./ 1 min | 100 |
| EPOXY X | 80 | | | | | |
| EPON 862 | 20 | 2P4MZ | Resorcinol | 30 | 225° C./ 1 min | 100 |
| EPOXY E | 80 | | | | | |
| EPON 862 | 20 | 2P4MZ | Bisphenol A | 30 | 225° C./ 1 min | 100 |
| EPOXY E | 80 | | | | | |

Example V

Performance Results of Adhesive Formulations

Several of the adhesive formulations from examples III and IV, and a snap-cure die attach formulation similar to those commercially available, containing 25% volume silver flakes were used to bond silicon dies to copper lead frames. These were snap-cured on a hot plate at 225° C. for one minute, and were fully cured as determined by DSC analysis.

The formulations were tested for die shear strength on silicon chips (80×80 mil$^2$) using a Hybrid Machine Products Corp, die shear tester (Model 1750)/ Chatillon DFI 50 digital force gauge. The force required to remove the bonded die was read in kg units, and converted to a die shear strength in MPa averaged over five samples. Tests were performed after cure (i) at room temperature (RT), (ii) at 250° C. after 250° C. for one minute (250° C., 1 min) (to simulate the wire bonding operation during manufacture), and (iii) after boiling in water for two hours, and then at 250° C. after 250° C. for one minute (100° C. $H_2O$; 250° C., 1 min) (intended to test resistance to moisture and the phenomenon known as "pop-corn", a mechanical failure of fully encapsulated packages after moisture exposure during solder reflow process, 220°–260° C.).

The formulations were also tested for radius of curvature (flexibility) at room temperature after curing and after curing followed by thermal shock (250° C. for one minute on a hot plate) on silicon chips (200×600 $mil^2$) using a Tokyo Seimitsu SURFCOM surface texture measuring instrument, reported in millimeter (mm) units, averaged over three samples.

The formulations and performance data are presented in Table V and show the snap-cured formulations maintained flexibility and good die shear strength at room temperature and after thermal shock; the die shear values obtained after exposure to moisture and thermal shock are within a range usable for die attach adhesives.

TABLE V

| SNAP CURE FORMULATION | | | DIE SHEAR (MPa) | | | RADIUS OF CURVATURE | |
|---|---|---|---|---|---|---|---|
| Composition parts by weight | | Epoxy Properties | RT | 250° C., 1 min | 100° C. $H_2O$, 2 hr 250° C., 1 min | RT | 250°C./ 1 min |
| EPOXY C | 80 | Tg = 60° C. | 23.7 | 1.4 | 1.1 | 420 mm | 350 mm |
| EPON 862 | 20 | WPE = 289 | cohesive | cohesive | cohesive | | |
| Novolak | 20 | V = 9100 cps | failure | failure | failure | | |
| EPOXY D | 80 | Tg = 52° C. | 14.3 | 1.4 | 1.2 | 480 mm | 420 mm |
| EPON 862 | 20 | WPE = 252 | cohesive | cohesive | cohesive | | |
| Novolak | 40 | V = 410 cps | failure | failure | failure | | |
| EPOXY E | 80 | Tg = 60° C. | 23.7 | 1.5 | 1.2 | 400 mm | 380 mm |
| EPON 862 | 20 | WPE = 241 | cohesive | cohesive | cohesive | | |
| Novolak | 40 | V = 347 cps | failure | failure | failure | | |
| FLEX EPOXY X | 80 | Tg = 28° C. | 17.7 | 1.2 | 0.8 | 550 mm | 470 mm |
| EPON 862 | 20 | WPE = 376 | cohesive | cohesive | cohesive | | |
| Novolak | 40 | V = 361 cps | failure | failure | failure | | |
| FLEX EPOXY X | 80 | Tg = 28° C. | 14.3 | 2.0 | | 320 mm | 320 mm |
| AROM | 20 | WPE = 376 | cohesive | cohesive | | | |
| EPOXY Y | | V = 361 cps | failure | failure | | | |
| Novolak | 40 | | | | | | |
| Control | | | 23.7 | 2.1 | 0.2 | 230 mm | 220 mm |

Notes:
(a) The epoxy equivalent weight (WPE, weight per epoxy) for each of the epoxy products was determined by dissolving the compound in glacial acetic acid followed by titration with standardized HBr/acetic acid (~0.1N) to the violet/green transition of crystal violet indicator.
(b) The viscosity of each of the samples was determined using a Brookfield cone-n-plate viscometer at multiple spindle speeds at 25° C. and is reported as an average of three readings.

Example VI

Effect of Aromatic Epoxy and Phenolic Hardener on Wet/Hot Strength

The effect of the level of aromatic epoxy and phenolic hardener on the die shear strength of a snap-cured formulation after exposure to boiling water for two hours and thermal shock on a hot plate at 250° C. was tested using representative formulations. The formulations and data are presented in Tables VIA and VIB. The data show that the higher the level of aromatic epoxy, and the higher the level of phenolic hardener, the better the wet/hot strength performance.

Table VI A

| Epoxy X (80 parts), EPON 862 (20 parts), 2E4MZ (5 pphr) Phenolic Novolak (parts per hundred parts resin) | | 0 | 10 | 20 | 30 | 40 | 50 |
|---|---|---|---|---|---|---|---|
| Die Shear (MPa)(80 × 80 $mil^2$) | | | | | | | |
| Room temperature | Die on lead frame | 0.8 | 12.4 | 18.1 | 24.4 | 31.4 | |
| 250° C., 1 min | Die on lead frame | 0.5 | 0.9 | 1.4 | 1.7 | 1.6 | |
| 250° C., 1 min 100° C. | Die on die | 0.5 | 1.2 | 2.2 | 2.2 | 2.3 | |

Table VI A-continued

| Epoxy X (80 parts), EPON 862 (20 parts), 2E4MZ (5 pphr) Phenolic Novolak (parts per hundred parts resin) | | 0 | 10 | 20 | 30 | 40 | 50 |
|---|---|---|---|---|---|---|---|
| H₂O, 2 hrs 250° C., 1 min | Die on lead frame | | 0.3 | 0.4 | 0.5 | 0.8 | 0.8 |
| Radius of Curvature (mm) (200 × 600 mil²) | | | | | | | |
| Room temperature | | | 2000 | 580 | 450 | 480 | 650 |
| 250° C., 1 min | | | 1900 | 590 | 430 | 430 | 550 |

TABLE VI B

| Epoxy X (60 parts), EPON 862 (40 parts), 2E4MZ (5 pphr) Phenolic Novolak (parts per hundred parts resin) | | 0 | 10 | 20 | 30 | 40 | 50 |
|---|---|---|---|---|---|---|---|
| Die Shear (MPa) (80 × 80 mil²) | | | | | | | |
| Room temperature | Die on lead frame | 7.6 | 10.3 | 15.2 | 19.3 | 24.4 | 31.4 |
| 250° C., 1 min | Die on lead frame | 0.5 | 0.6 | 1.2 | 1.8 | 1.7 | 1.6 |
| 250° C., 1 min 100° C. | Die on die | 0.8 | 0.9 | 1.2 | 1.8 | 2.2 | 2.3 |
| H₂O, 2 hrs 250° C., 1 min | Die on lead frame | | 0.3 | 0.4 | 1.1 | 1.6 | |
| Radius of Curvature (mm) (200 × 600 mil²) | | | | | | | |
| Room temperature | | | 510 | 430 | 360 | 300 | |
| 250° C., 1 min | | | 680 del | 460 | 350 | 300 | |

Notes on table: del = delaminated

Example VII

Syntheses of Representative Flexible Epoxies

ADDUCT A:

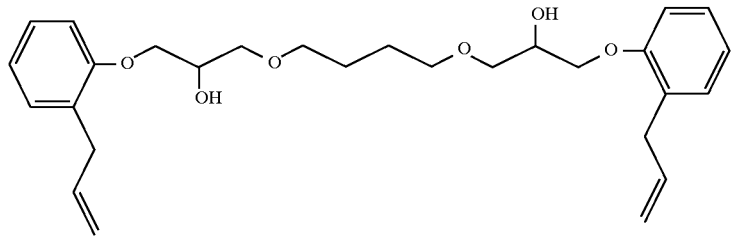

The reaction apparatus was a 500 ml round bottom flask equipped with a mechanical stirrer, thermometer, and condenser. The reagents, 2-allyl phenol (159 gms, 1.19 moles), 1,4-butanediol diglcidyl ether (120 gms, 0.59 moles), and 1% tetramethylammonium chloride catalyst (2.5 gms), were added to the reaction apparatus and stirred at 50° C. for approximately an hour. The temperature was raised to 70° C. and the reagents stirred at that temperature for an additional hour; then the temperature was raised to 120° C. and the reagents held at that temperature while progress of the reaction was monitored by gas chromotograpy (CC). Completion was determined to occur after four hours, at which time the reaction was cooled and the work-up initiated.

The reaction mixture was transferred to a single neck flask and placed on a kugelrohr apparatus (120° C./0.1 mmHg) to strip off any residual starting materials (particularly, 2-allyl phenol).

The adduct was transferred to a 1000 ml separatory funnel and dissolved in 300 ml of toluene. This organic phase was washed with 5% sodium carbonate (3×200 mL), 10% sodium sulfate (3×200 mL), and then passed through a neutral alumina pad (~200 mL) rinsed with toluene.

The toluene was stripped off by rotory evaporator at 60° C./25 mm Hg vacuum, and then placed on a kugelrohr at 70° C./0.1 mm Hg to remove any residual solvent.

The adduct was obtained in 90% yield, and was characterized by IR and ¹H NMR spectroscopy. It had a viscosity ranging from 650 to 870 cps at 25° C.

ADDUCT B:

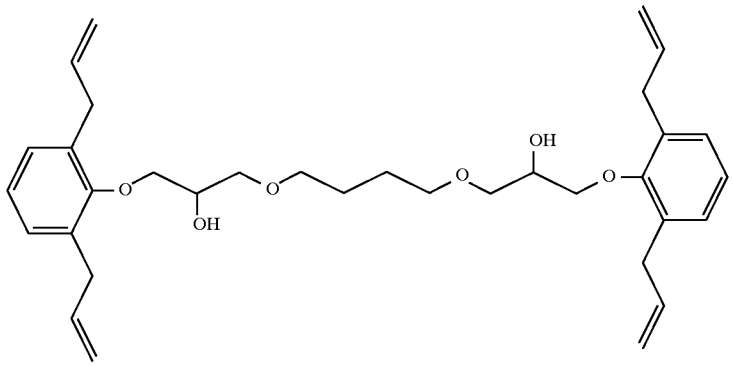

Adduct B was prepared in a manner similar to that used for Adduct A, except that 2,6-diallyl phenol (310 gms, 1.78 moles) was reacted with 1,4-butanediol diglycidyl ether (180 gms, 0.89 moles) in the presence of 4.5 gm tetramethylammonium chloride. The temperature of the reaction mixture was gradually raised to 180° C. and held there for one hour until reaction was complete as indicated by GC. The product was isolated as described for Adduct A in 81% yield and was characterized by IR and $^1$HNMR spectroscopy. It had a viscosity of 983 cps at 25° C.

The reaction apparatus was a one liter multi-neck flask equipped with mechanical stirrer, thermometer, Dean-Stark trap, and condenser. Solid sodium hydroxide pellets (19.95 gm, 0.5 moles) and 83 mL xylene under a gentle nitrogen purge were added to the apparatus and heated with a heating mantle to 70° C. At that temperature 2-allyl phenol (66.9 gm, 0.5 moles) dissolved in 200 mL xylene was introduced through a slow-addition funnel, while the system was brought to reflux. The water formed as a by-product was driven off via azeotropic distillation to the Dean-Stark trap, followed by distillation of additional xylene (225 mL) through the Dean-Stark trap to remove any trapped water.

ADDUCT C:

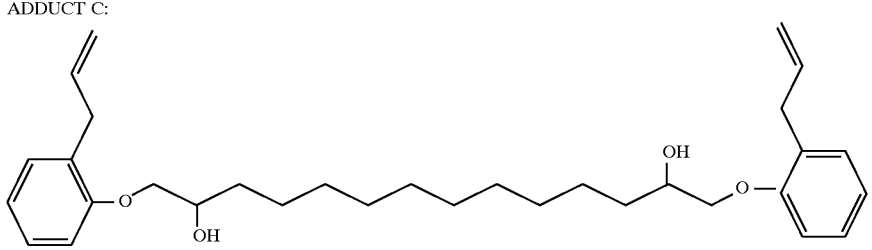

Adduct C was prepared in a manner similar to that used for Adduct A, except that 2-allylphenol (8.44 gm, 0.063 moles) was reacted with 1,2,13,14-diepoxy tetradecane (6.48 gm, 0.0286 moles; prepared by the oxidation of 1,13-tetradecadiene) in the presence of 0.1 gm tetramethylammonium chloride. The reaction mixture was heated to 185° C. and held at that temperature for 3.3 hour until reaction was complete as indicated by GC. The product was isolated as described for Adduct A in 81% yield and was characterized by IR and $^1$HNMR spectroscopy.

Then 125 mL p-cymene, 25 mL dimethylformamide, and 0.1 gm KI were added and the entire contents cooled to 100° C. The dichloride of poly(tetrahydrofuran)-250 (45 gm, 0.17 mole; prepared by the action of thionyl chloride on poly (tetrahydrofuran)- 250, which is available from BASF Corp.) dissolved in 50 mL p-cymene was introduced into the flask through a slow-addition funnel. The reaction temperature was raised to 150° C. and held for 24 hours. Upon cooling, the by-product salts (sodium chloride) were removed by filtration, and the filtrate was washed with 5%

ADDUCT D:

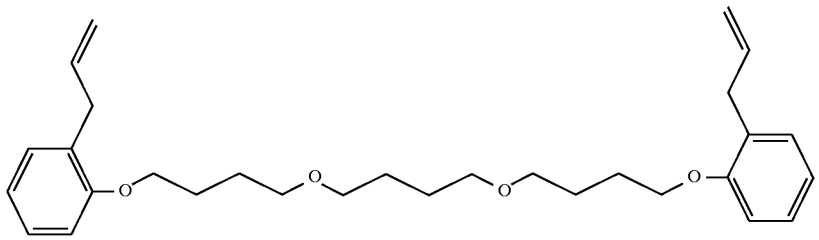

sodium hydroxide (2×150 mL), and then 10% sodium sulfate (150 mL each) until the pH became neutral (pH=7 on test strip).

The solvent was removed first on a rotory evaporator, then on a Kugelrohr apparatus (130° C./0.2 mm Hg). The product was collected in 95% yield and was analyzed by IR and $^1$HNMR spectroscopy.

ADDUCT E:

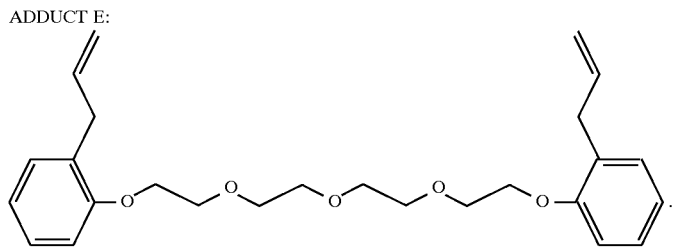

The reaction apparatus was a five liter multi-neck flask equipped with mechanical stirrer, thermometer, Dean-Stark trap, and condenser. Solid sodium hydroxide pellets (79.2 gm, 1.98 moles) and one liter xylene were added to the reaction apparatus under a gentle nitrogen purge, and heated with a heating mantle to 135° C. (reflux). At that temperature 2-ally phenol (267 gm, 1.98 moles) was introduced through a slow-addition funnel, while the system was maintained at reflux. The water formed as a by-product was driven off via azeotropic distillation to the Dean-Stark trap, followed by distillation of 100 mL additional xylene through the Dean-Stark trap to remove any trapped water.

The internal temperature was lowered to 90° C., and 100 mL dimethylformamide and tetraethylene glycol ditosylate (400 gm, 0.795 moles; prepared by the action of p-toluenesulfonyl chloride on tetraethylene glycol in the presence of pyridine) dissolved in 300 mL xylene were introduced into the flask through a slow-addition funnel. The reaction temperature was raised to 120° C. and held there for two hours. The reaction was cooled and the by-product salts (sodium tosylate) were removed by filtration. The filtrate was washed with 5% sodium hydroxide (2×600 mL), then washed with 10% sodium sulfate (3×300 mL) until the pH became neutral (pH=7 on test strip).

The solvent was removed first on a rotory evaporator, then on a Kugelrohr apparatus (80° C./0.2 mm Hg). The product was collected in 95% yield and analyzed by IR and $^1$HNMR spectroscopy.

EPOXY A:

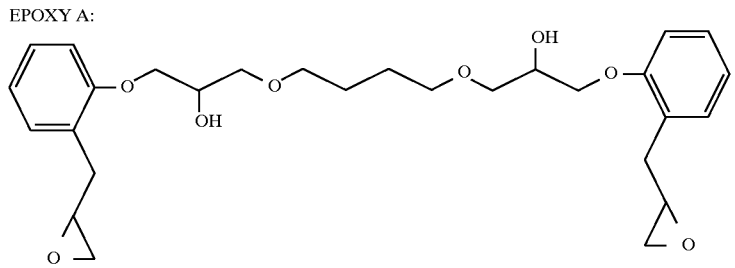

Adduct A was oxidized to give Epoxy A by two methods: with peracetic acid and with peroxyimidic acid.

1. Oxidation with Peracetic Acid

The reaction apparatus was a 500 ml flask equipped with mechanical stirrer, thermometer and slow-add funnel.

Adduct I (75 gms, 0.16 moles, 0.32 moles of olefinic functionality), 1,2-dichloroethane (150 mL) and sodium acetate (4.7 gms) was added to the reaction apparatus and brought to 23° C. using a water bath. Introduction of peracetic acid (94.7 gms) (35% in acetic acid) was begun, and the reaction exothermed to 29° C. After addition was completed, the water bath was warmed to 30° C. The internal temperature rose to 38° C. After 10 minutes the temperature dropped to 35° C. and was held steady at 35°0 C. for 5 hours. The reaction was monitored for completion by IR spectroscopy for the disappearance or minimization of the 1635 cm$^{-1}$ absorption.

At completion, 300 mL of distilled water was added to the reaction mixture. The phases were separated, and the organic phase washed with 300 mL 5% sodium bicarbonate solution, then with 200 mL of 5% sodium sulfite solution. Toluene (300 mL) was added to break the emulsion. The organic layer was then washed with 200 mL of 10% sodium sulfate, and 200 mL of distilled water.

The organic was separated off, dried over magnesium sulfate and suction filtered. The solvent was stripped off first on the rotory evaporator (50° C./20 mmHg) and then on a Kugelrohr apparatus (60° C./0.1 mmHg). The final product was isolated as an oil, and characterized by a viscosity of 7280 cps at 25° C., an epoxy equivalent weight=269 (theoretical value=251), and by IR and $^1$H NMR spectroscopy.

2. Oxidation with Acetonitrile/Hydrogen Peroxide (Peroxyimidic acid)

The reaction apparatus was a 250 ml round bottom flask equipped with mechanical stirrer, thermometer, and slow-add funnel. Adduct I (30.0 gm, 0.0638 moles, 0.128 moles olefin functionality), methanol (74 mL), acetonitrile (11.54 gm, 0.2815 moles), and KHCO$_3$ (7.12 gm, 0.7111 mole)

were added to the apparatus and heated to 40° C. At that temperature 30% $H_2O_2$ (10.0 gm, 0.0882 mole) was added dropwise. The reaction mixture was maintained at 40° C. for seven hours, at which point, additional 30% $H_2O_2$ (13.8 gm, 0.1218 mole) was added dropwise. The reaction was maintained at 40° C. for a further 20 hours.

Then 2,2-dimethoxypropane (48 gm, 0.462 mole, or 0.5 equivalent based on $H_2O$ charged from 30% hydrogen peroxide) was added dropwise. The reaction was heated at 40° C. for an additional 24.5 hours, corresponding to the point at which the IR trace of a reaction sample indicated minimal 1637 $cm^{-1}$ absorbance.

The peroxide was neutralized by the addition of 10% $Na_2SO_3$ as determined by KI-starch indicator test strip. The methanol and acetonitrile were removed in vacuo on the rotor evaporator (40° C./25 mm HG). The residue was taken up in 150 mL toluene and washed with distilled water (150 mL). Emulsification was alleviated by the addition of 10% $Na_2SO_4$. The organic layer was separated and the solvent removed first on a rotory evaporator (80° C./25 mmHg), then on a Kugelrohr apparatus (80° C./0.1 mmHg).

The product was isolated at 74% yield (23.7 gm), characterized by an epoxy equivalent weight=315 (theoretical value=251), viscosity=6270 cps at 25° C., IR, and $^1H$ NMR spectroscopy.

The product was isolated in 85% yield and characterized by an epoxy equivalent weight=176 (theoretical value=154), viscosity=24,300 cps at 25° C., and by IR and $^1H$ NMR spectroscopy.

2. Oxidation with Acetonitrile/Hydrogen Peroxide (Peroxyimidic acid)

Adduct B was oxidized using acetonitrile and hydrogen peroxide as described for the synthesis of Epoxy A. The acetonitrile and hydrogen peroxide generated in situ the peroxyimidic acid. Adduct B (150 gm, 0.27 mole) was treated with acetonitrile (97 gm), potassium bicarbonate (60.5 gm), 30% hydrogen peroxide (200 gm), 2,2-dimethoxypropane (812.5 gm), and methanol (375 mL). The reaction was carried out at 40° C. until the IR absorption at 163 $cm^{-1}$ no longer changed significantly. The product was isolated in 74% yield, and was characterized by an epoxy equivalent weight=229 (theoretical value=154), viscosity=20,900 cps at 25° C., and by IR and $^1H$ NMR spectroscopy.

EPOXY B:

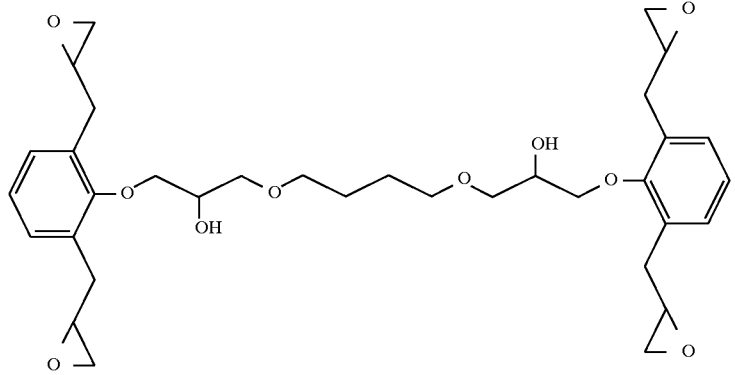

Adduct B was oxidized to give Epoxy B by two methods: with peracetic acid and with peroxyimidic acid.

EPOXY C:

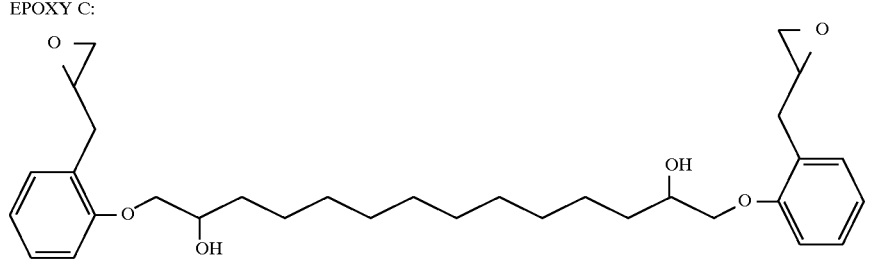

1. Oxidation with Peracetic Acid

Adduct B was oxidized using 35% peracetic acid as described for the synthesis of Epoxy A. Adduct B (110 gm, 0.2 mole) was treated with peracetic acid (210 mL of 35% solution, 1.09 moles) in 220 mL 1,2-dichloroethane at 35° C.

Adduct C was oxidized to give Epoxy C using peroxytungstate catalysis.

Oxidation with Peroxytungstate: Adduct C (17 gm, 0.035 mole) was dissolved in 60 mL dichloroethane to which was added 3.8 gm tetrabutylammonium hydrogen sulfate, and this was stirred vigorously at room temperature. To this rapidly stirred solution was added an aqueous mixture comprising sodium tungstate dihydrate (6.3 gm) in 10 mL distilled water with a sufficient amount of 85% phosphoric acid to adjust the pH to 6.5. Then 30% hydrogen peroxide (15.7 gm, 0.138 mole) was added at room temperature and the combined contents were stirred for 96 hours. At that point, the 1637 cm$^{-1}$ absorption in the IR spectrum was minimized.

The product was isolated by separating the phases and washing the organic layer with 5% sodium sulfite (2×100 mL) until the peroxide was completely quenched. The solvent was removed on a rotory evaporator at a temperature less than or equal to 40° C. and the residue dissolved in 100 mL toluene. The toluene layer was washed with 150 mL 5% sodium carbonate, with water (2×150 mL), then with 10% sodium sulfate (2×150 mL). The toluene was removed from the organic layer first on a rotory evaporator, then on a Kugelrohr apparatus under high vacuum (80° C./0.1 mm Hg). The product was an oil isolated at 93% yield, and was characterized by an epoxy equivalent weight=289 (theoretical value=263), viscosity=9100 cps at 25° C., and by IR and $^1$H NMR spectroscopy.

Adduct E was oxidized to Epoxy E by two methods: with peracetic acid and with peroxytungstate catalysis.

1. Oxidation with Peracetic Acid

Adduct E (30 gm, 0.07 mole) was oxidized as described in the synthesis of Epoxy A using 35% peracetic acid at 35° C. in 1,2-dichloroethane. The product was isolated as an oil in 91% yield and was characterized by an epoxy equivalent weight=258 (theoretical value=229), viscosity=397 cps at 25° C., and by IR and $^1$H NMR spectroscopy.

2. Oxidation with Peroxytungstate catalysis

Adduct E (24 gm, 0.056 mole) was oxidized as described in the synthesis of Epoxy C using sodium tungstate dihydrate and hydrogen peroxide. The product was isolated as an oil in 94% yield, and was characterized by an epoxy equivalent weight=241 (theoretical value=229), viscosity= 347 cps at 25° C., and by IR and $^1$H NMR spectroscopy.

Example VIII

Measure of Chlorine Content

Test Method: The amount of hydrolyzable chlorine was determined by the following method: Weigh accurately 1–5 g (to the nearest 0.1 mg) of resin into a clean, 125 ml Erlenmeyer flask with a Teflon® coated magnetic stir bar. Add 40 ml of 0.1N KOH dissolved in methanol. Place flask fitted with reflux condensor into a water bath heated by magnetic stirrer/hot plate unit. Reflux the stirred solution for exactly 15 minutes, then remove the flask, and allow it to cool to room temperature. Transfer the liquid into a clean 250 ml beaker. Rinse the sample flask three times with 50 ml portions of methanol, transferring the liquid into the beaker. Add 10 ml of glacial acetic acid and titrate the chloride ion potentiometrically to the end point with 0.005N AgNO$_3$ solution. Calculate the hydrolyzable chloride content in ppm as follows:

EPOXY D:

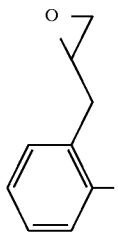
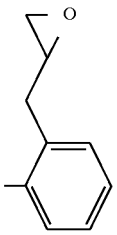

Adduct D was oxidized to Epoxy D by two methods: with peracetic acid and with peroxytungstate catalysis.

1. Oxidation with Peracetic Acid

Adduct D (50 gm, 0.107 mole) was oxidized as described in the synthesis of Epoxy A using 35% peracetic acid at 35° C. in 1,2-dichloroethane. The product was isolated as an oil at 60% yield, and was characterized by an epoxy equivalent weight=274 (theoretical value=249), viscosity=417 cps at 25° C., and by IR and $^1$H NMR spectroscopy.

2. Oxidation with Peroxytungstate catalysis

Adduct D (67.8 gm, 0.14 mole) was oxidized as described in the synthesis of Epoxy C using sodium tungstate dehydrate and hydrogen peroxide. The product was isolated as an oil in 83% yield, and was characterized by an epoxy equivalent weight=252 (theoretical value=249), viscosity= 410 cps at 25° C., and by IR and $^1$H NMR spectroscopy.

EPOXY E:

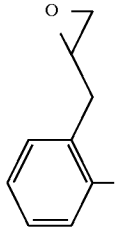
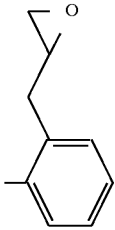

$$\text{Chloride } (ppm) = \frac{(\text{ml } titrant)\,(\text{N AgNO}_3)\,(3.55 \times 10^4)}{\text{weight sample g}}$$

The amount of total chlorine was determined by the following method: Accurately weigh 1–5 g (to the nearest 0.1 mg) of resin into a clean Erlenmeyer flask with a magnetic stir bar. Add 30 ml of dioxane and 15 ml of 3N KOH solution in ethanol. Place flask fitted with a reflux condenser into a 100° C. water bath heated on a stirrer/hot plate unit. Allow sample solution to reflux for 30 minutes. Remove flask and allow it to cool to room temperature. Transfer the liquid into a clean 400 ml beaker. Rinse the sample flask three times with 50 ml portions of methanol, transferring the liquid into the beaker. Add 100 ml of glacial acetic acid. Titrate potentiometrically with 0.005N AgNO$_3$ solution to the end point using a silver electrode with a KNO$_3$ salt bridge. Calculate the chloride content in ppm as described above.

EPOXY F, comparative example:

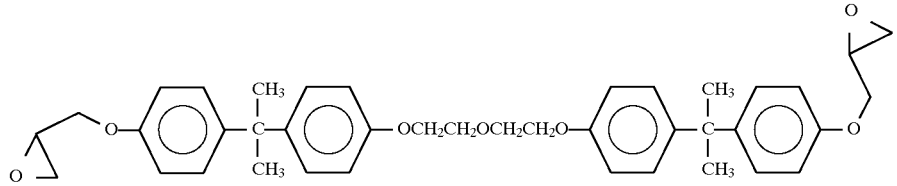

As a comparison to the inventive examples, Epoxy F was prepared according to the methods described in U.S. Pat. No. 3,522,210, issued to Sellers, examples 1A and 15.

Preparation of bisphenol compound (example 1): To a one liter flask with mechanical stirrer, thermometer, slow addition funnel, condenser, and nitrogen blanket was charged bisphenol A (228.29 g, 1.0 mole), 150 g dimethyl sulfoxide (DMSO), and 150 g toluene. After the solid dissolved a solution of 50% aqueous NaOH (80 g, 1.0 mole) was added over 20 minutes. The temperature rose to about 50° C. and heat was applied to raise the temperature to 100°–110° C. Reflux was achieved at 101° C. at which point 2-chloroethyl ether (71.5 g, 58.6 mL, 0.5 mole) was added through the slow addition funnel over 18 minutes. The reaction temperature was held at reflux for 36.75 hours at which point the pH still did not reach 7–8 but GC analysis indicated the reaction had stalled with respect to consumption of bisphenol A. Toluene (150 mL) was added and azeotropic distillation was initiated to drive off ~60 mL H$_2$O and another 40 mL of toluene was driven off additional to ensure dryness. The organic solution was filtered, neutralized to pH=6 with conc. HCl, and refiltered. The solution was placed in a single-neck round bottom flask and stripped on a rotary evaporator to 60° C./11 mmHg, collecting 300 mL distillate. Further distillation was carried out at atmospheric pressure (~760 mmHg) and 170° C. pot temperature, then establishing vacuum to ~30 mmHg and raising the pot temperature to 219° C. (vapor temperature to 122° C.). The flask was cooled to room temperature.

Preparation of Diglycidyl Ether with Flexible Linkage (example 15): The material was dissolved in 400 g ethanol and 240 mL epichlorohydrin in order to transfer to a 2 liter multi neck flask for the second reaction. This solution was heated to 60° C. at which point the addition of 50% NaOH (1.25 mole) 70 mL was conducted as prescribed (~7 mL over 25 min., ~10 mL over 5 min., ~46 mL over 35 min., and ~7 mL over 15 min.). The reaction mixture was transferred to a 2-liter single neck flask and ethanol, water, and epichlorohydrin were removed on a rotary evaporator to 96° C./11 mmHg. The residue was dissolved in 600 mL methyl isobutyl ketone and 800 mL water, transferred to a separatory funnel and the phases separated. The organic layer was washed with 200 mL water, which resulted in an emulsion that was alleviated by the addition of 100 mL saturated sodium sulfate. The pH of the aqueous wash was ~7 (neutral). The organic solution was placed on the rotary evaporator to remove solvent to 95° C./11 mmHg. The material was further stripped on a Kugelrohr apparatus to 133° C./1.5 mmHg. The product, a dark amber material with a stringy taffy-like consistency, was isolated in 89% yield, and was characterized as having an epoxy equivalent weight as WPE=357.5, hydrolyzable chlorine=435 ppm, bound chlorine=2103 ppm, and total chlorine=2538 ppm.

SUMMATION OF CHLORINE DATA:

| EPOXY | Hydrolyzable Chlorine (ppm) | Total Chlorine (ppm) | Bound Chlorine (ppm) |
|---|---|---|---|
| A-1 | 519 | 719 | 200 |
| A-2 | 455 | 564 | 109 |
| B-1 | 467 | 620 | 153 |
| B-2 | 624 | 839 | 215 |
| C | 883 | 959 | 76 |
| D-1 | 35 | 103 | 68 |
| D-2 | 53 | 100 | 47 |
| E-1 | none detected | 785 | 785 |
| E-2 | 58 | 578 | 520 |
| F-Comparative | 435 | 2538 | 2103 |

In comparing the inventive epoxy compounds with prior art compound F, it will be noted that the hydrolyzable chlorine content is similar, and it is further noted that there are methods described in the literature for treatment of the epoxide containing molecule to reduce this value. (See, for example, U.S. Pat. No. 4,785,061, which discusses at column 2 hydrolyzable chlorine, bound chlorine, and total chlorine.) Nevertheless, the total chlorine value is critical when considering the prevention of corrosion of sensitive microcircuitry conductive lines, and reported methods lower but do not effectively remove this chlorine contaminant from an epichlorohydrin based synthetic route.

We claim:

1. An adhesive formulation for microelectronics use comprising in parts by weight:

(i) 20–80 parts of a liquid epoxy resin having a center flexible portion, characterized in that it has a total chlorine content of less than 0.1% by weight and the general structure:

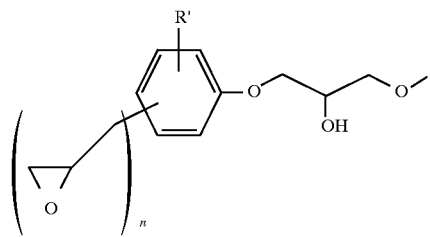

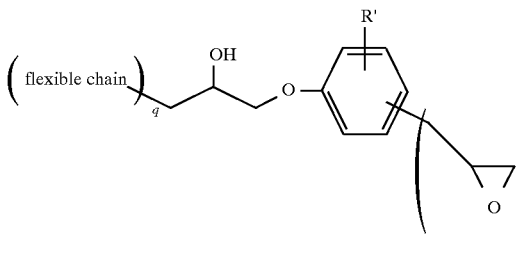

in which:
R' is H, $C_{1-18}$alkyl, $C_{1-15}$alkoxy, aryl or alkylaryl, $C_{1-5}$perfluoroalkyl, $C_{1-5}$acyl;
n is an integer 1–3; and
the flexible chain is $CH_2CH_2CH_2O$ and q is an integer 1–10, $CH_2CH_2O$ and q is an integer 3–10, or $CH_2$ and q is an integer 6–20; and (ii) 80–20 parts of an aromatic O-glycidyl ether resin having one or more aromatic rings, the aromatic rings substituted with two or more O-glycidyl ether groups and optionally one or more $C_{1-3}$ groups, the aromatic O-glycidyl ether having an epoxy equivalent weight (WPE, weight per epoxy) of 200 or less, the total parts of (i) and (ii) to equal 100 parts by weight, and
(iii) a curing catalyst, and
(iv) optionally, a conductive filler.

2. The adhesive formulation according to claim 1 in which the flexible chain is $CH_2CH_2CH_2O$ and q is an integer 1–6, or $CH_2CH_2O$ and q is an integer 3–10.

3. The adhesive formulation according to claim 1 in which the flexible liquid epoxy resin has the general structure:

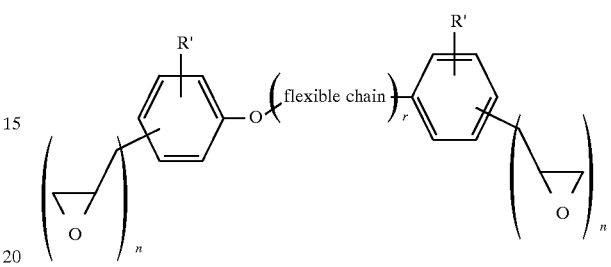

in which:
R' is H, $C_{1-18}$alkyl, $C_{1-5}$alkoxy or aryl or alkylaryl, $C_{1-5}$perfluoroalkyl, or $C_{1-5}$acyl; and
n is an integer 1–3; and
the flexible chain is $CH_2CH_2CH_2CH_2O$ when r is an integer 1–10; or
the flexible chain is $CH_2CH_2O$ when r is an integer 3–10; or
the flexible chain is $CH_2$ when r is an integer 10–20.

4. The adhesive formulation according to claim 1 in which the flexible epoxy resin is selected from the group of flexible epoxy resins consisting of:

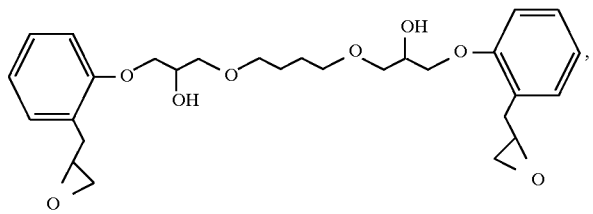

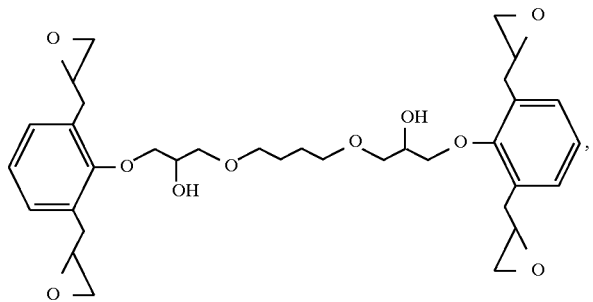

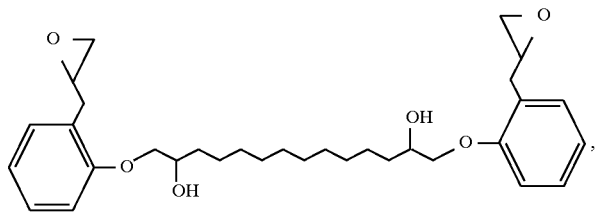

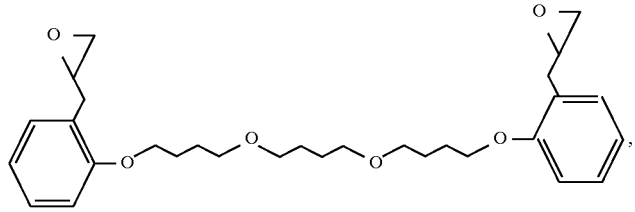

and

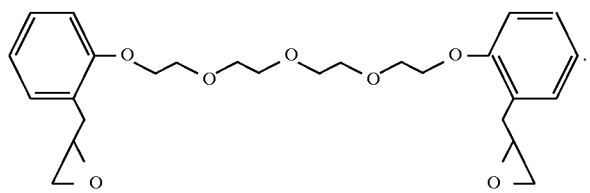

5. The adhesive formulation according to claim 1 in which the liquid epoxy resin with the flexible chain is present in an amount of 40–80 parts by weight, and the aromatic O-glycidyl ether resin is present in an amount of 60–20 parts by weight, to a total of 100 parts by weight.

6. The adhesive formulation according to claim 1 in which the aromatic O-glycidyl ether resin is selected from the group consisting of bisphenol-F diglycidyl ether, bisphenol-A diglycidyl ether, resorcinol diglycidyl ether, and epoxy phenol novolak.

7. The adhesive formulation according to claim 1 in which the curing catalyst is selected from the group consisting of imidazole, 2-ethylimidazole, 2-ethyl-4-methylimidazole, 2-phenylimidazole, 2-phenyl-4-methylimidazole, and 2-undecylimidazole.

8. The adhesive formulation according to claim 1 in which the curing catalyst is present in an amount of about 5 parts by weight per hundred parts by weight resin.

9. The adhesive formulation according to claim 1 in which the conductive filler is silver flakes and is present in an amount of about 25% by volume of the adhesive formulation.

10. The adhesive formulation according to claim 2 in which the liquid epoxy resin with the flexible chain is present in an amount of 40–80 parts by weight, and the aromatic O-glycidyl ether resin is present in an amount of 60–20 parts by weight, to a total of 100 parts by weight.

11. The adhesive formulation according to claim 3 in which the liquid epoxy resin with the flexible chain is present in an amount of 40–80 parts by weight, and the aromatic O-glycidyl ether resin is present in an amount of 60–20 parts by weight, to a total of 100 parts by weight.

12. The adhesive formulation according to claim 4 in which the liquid epoxy resin with the flexible chain is present in an amount of 40–80 parts by weight, and the aromatic O-glycidyl ether resin is present in an amount of 60–20 parts by weight, to a total of 100 parts by weight.

13. The adhesive formulation according to claim 2 in which the aromatic O-glycidyl ether resin is selected from the group consisting of bisphenol-F diglycidyl ether, bisphenol-A diglycidyl ether, resorcinol diglycidyl ether, and epoxy phenol novolak.

14. The adhesive formulation according to claim 3 in which the aromatic O-glycidyl ether resin is selected from the group consisting of bisphenol-F diglycidyl ether, bisphenol-A diglycidyl ether, resorcinol diglycidyl ether, and epoxy phenol novolak.

15. The adhesive formulation according to claim 4 in which the aromatic O-glycidyl ether resin is selected from the group consisting of bisphenol-F diglycidyl ether, bisphenol-A diglycidyl ether, resorcinol diglycidyl ether, and epoxy phenol novolak.

16. The adhesive formulation according to claim 2 in which the curing catalyst is selected from the group consisting of imidazole, 2-ethylimidazole, 2-ethyl4-methylimidazole, 2-phenylimidazole, 2-phenyl-4-methylimidazole, and 2-undecylimidazole.

17. The adhesive formulation according to claim 3 in which the curing catalyst is selected from the group consisting of imidazole, 2-ethylimidazole, 2-ethyl-4-methylimidazole, 2-phenylimidazole, 2-phenyl-4-methylimidazole, and 2-undecylimidazole.

18. The adhesive formulation according to claim 4 in which the curing catalyst is selected from the group consisting of imidazole, 2-ethylimidazole, 2-ethyl-4-methylimidazole, 2-phenylimidazole, 2-phenyl-4-methylimidazole, and 2-undecylimidazole.

19. The adhesive formulation according to claim 2 which the curing catalyst is present in an amount of about 5 parts by weight per hundred parts by weight resin.

20. The adhesive formulation according to claim 3 in which the curing catalyst is present in an amount of about 5 parts by weight per hundred parts by weight resin.

21. The adhesive formulation according to claim 4 in which the curing catalyst is present in an amount of about 5 parts by weight per hundred parts by weight resin.

22. The adhesive formulation according to claim 2 in which the conductive filler is silver flakes and is present in an amount of about 25% by volume of the adhesive formulation.

23. The adhesive formulation according to claim 3 in which the conductive filler is silver flakes and is present in an amount of about 25% by volume of the adhesive formulation.

24. The adhesive formulation according to claim 4 in which the conductive filler is silver flakes and is present in an amount of about 25% by volume of the adhesive formulation.

* * * * *